(12) United States Patent
Lavi et al.

(10) Patent No.: US 7,321,676 B2
(45) Date of Patent: Jan. 22, 2008

(54) AUTOMATIC DETERMINATION OF THE LONG AXIS OF THE LEFT VENTRICLE IN 3D CARDIAC IMAGING

(75) Inventors: Guy A. Lavi, Giv'atayim (IL); Jonathan Lessick, Haifa (IL)

(73) Assignee: Koninklijke Philips Electronics N.V., Eindhoven (NL)

( * ) Notice: Subject to any disclaimer, the term of this patent is extended or adjusted under 35 U.S.C. 154(b) by 716 days.

(21) Appl. No.: 10/859,427

(22) Filed: Jun. 2, 2004

(65) Prior Publication Data

US 2005/0288598 A1 Dec. 29, 2005

Related U.S. Application Data

(60) Provisional application No. 60/491,006, filed on Jul. 30, 2003.

(51) Int. Cl.
*G06K 9/00* (2006.01)
(52) U.S. Cl. .................... 382/128; 382/308; 378/21
(58) Field of Classification Search ............... 382/100, 382/128, 129, 130, 131, 132, 154, 168, 172, 382/191, 194, 237, 201–203, 242, 274, 276, 382/285–291, 305, 133, 181, 224, 232, 308; 600/443, 409; 378/21, 20
See application file for complete search history.

(56) References Cited

U.S. PATENT DOCUMENTS

| | | | | |
|---|---|---|---|---|
| 5,421,331 | A | 6/1995 | Devito et al. ............... 128/659 |
| 5,570,430 | A | 10/1996 | Sheehan et al. ............ 382/128 |
| 5,617,459 | A | 4/1997 | Makram-Ebeid et al. ..... 378/62 |
| 5,734,739 | A | 3/1998 | Sheehan et al. ............ 382/128 |
| 5,871,019 | A | 2/1999 | Belohlavek ................. 128/916 |
| 6,065,475 | A | 5/2000 | Qian et al. .................. 128/659 |
| 6,187,032 | B1 * | 2/2001 | Ohyu et al. ................. 600/409 |
| 6,289,135 | B1 | 9/2001 | Declerck et al. ........... 328/276 |
| 6,366,684 | B1 * | 4/2002 | Gerard et al. ............... 382/132 |
| 6,438,403 | B1 | 8/2002 | Cline et al. ................. 600/410 |
| 6,447,452 | B1 * | 9/2002 | Liu et al. .................... 600/443 |
| 6,816,607 | B2 * | 11/2004 | O'Donnell et al. ......... 382/131 |
| 7,155,042 | B1 * | 12/2006 | Cowan et al. .............. 382/128 |

OTHER PUBLICATIONS

Cauvin, et al., "Automatic Detection of the Left Ventricular Myocardium Lonq Axis and Center in Thallium-201 Sinqle Photon Emission Computed Tomo ra h" Eur. J. Nucl. Med. 1992 19(121:1032-7.*

(Continued)

*Primary Examiner*—Seyed Azarian

(57) ABSTRACT

A diagnostic imaging apparatus generates a three-dimensional diagnostic image representation. The image representation is converted into an image representation of the patient's heart. A left lower posterior point of the heart image representation is selected as a first approximation of a left ventricle apex and a line of preselected orientation is drawn through the first approximation apex as a first approximation ventricle axis. The ventricle axis is redefined by generating short axis slices across the approximated ventricle axis, isolating a selected one of the ventricles, determining a centroid of each short axis slice of the selected ventricle, and fitting the axis to the apex approximation and the centroids. The apex location is redefined by looking for the lowermost short axis slice orthogonal to the redefined axis which intersects the ventricle volume and selecting the intersection point as the next approximation of the apex. The axis and apex redefining are iteratively repeated to determine the ventricle axis and apex automatically.

30 Claims, 3 Drawing Sheets

OTHER PUBLICATIONS

Janicki, et al., "Three-Dimensional Myocardial and Ventricular Shape: A Surface Representation", Am. J. Physiol. Jul. 1981: 241(1):H1-11.

DeKemp, et al., "Automated Determination of the Left Ventricular Long Axis In Cardiac Positron Tomography", Physiol. Meas. May 1996; 17(2):95-108.

Cauvin, et al., "Automatic Detection of the Left Ventricular Myocardium Long Axis and Center in Thallium-201 Single Photon Emission Computed Tomography", Eur. J. Nucl. Med. 1992 19(12):1032-7.

Germano, et al., "Automatic Reorientation of Three-Dimensional, Transaxial Myocardial Perfusion SPECT Images", J. Nucl. Med. Jun. 1995 36(6):1107-14.

Van Hastenberg, et al., "On the Generation of Short-Axis and Radial Long-Axis Slices in Thallium-201 Myocardial Perfusion Single-Photon Emission Tomography", Eur. J. Nucl. Med. Aug. 1996; 23(8):924-31.

* cited by examiner

AUTOMATIC DETERMINATION OF THE LONG AXIS OF THE LEFT VENTRICLE IN 3D CARDIAC IMAGING

CROSS REFERENCE TO RELATED APPLICATIONS

This application claims the benefit of U.S. provisional application Ser. No. 60/491,006 filed Jul. 30, 2003.

The present invention relates to the anatomical imaging arts. It finds application in conjunction with the automated determination of the left ventricle long axis. However, it is to be appreciated that it will also find application in conjunction with the determination of other dimensions of the left ventricle, the right ventricle, and other cardiac and anatomical regions. Although described with particular reference to CT tomography, it will further be appreciated that the invention is equally applicable to other diagnostic imaging techniques which generate two and three-dimensional digital diagnostic images for analysis.

In the past, CT scanners have been used to generate volumetric images of the patient's heart. With appropriate triggering or gating, CT images of a selected cardiac phase or a series of cardiac phases are readily generated. Although a three-dimensional electronic image representation is generated, the radiologist typically views a two-dimensional display. More specifically, the radiologist typically views slices or planes through the volume of data.

One of the characteristics of the heart that is of medical significance is the length of the long axis of the left ventricle. The diagnosing physician selects imaging planes through the left ventricle from which the length of the left ventricle axis is manually measured. Defining the ventricle's principal coordinate system allows the physician to evaluate the heart, particularly left ventricular geometry and function, by predetermined and conventional methods. One major use includes using the long axis determination as a baseline for heart, particularly left ventricle, function assessments.

One of the drawbacks to manual measurement is that it can be inconsistent or inaccurate. The left ventricle typically lies along a skewed axis, relative to the orthogonal coordinate system which is defined by the sagittal, longitudinal, and transverse directions of a conventional CT scan. If the imaging slice on which the measurement is made is not coplanar with the long axis of the left ventricle, the measurement will be inaccurate. Imaging planes which are skewed or offset from the long axis do not accurately depict the length or direction of the left ventricle long axis.

An automated left ventricle measurement technique has been proposed for PET studies. This technique is based on the myocardiogram of the left ventricle, rather than the actual blood cavity. It assumes that the left ventricle has a symmetric ellipsoidal geometry and that the radiopharmaceutical uptake by the surrounding myocardiogram will be homogeneous. These assumptions are not necessarily correct, particularly in diseased ventricles.

The present application contemplates a new and improved measurement technique which automatically and accurately determines the long axis and other physical characteristics of the heart and other chambers.

In accordance with one aspect of the present invention a morphological system for determining physiological characteristics of a patient's heart from a digital diagnostic image representation is disclosed. A cardiac morphology processor processes the diagnostic image representation into a heart blood volume image representation. A ventricle apex approximation processor determines an approximation of an apex of one of the ventricles. A ventricle axis approximation processor determines an approximation of an axis of the ventricle as a line which axis intersects the ventricle apex. A ventricle axis redefining processor redefines the approximation of the ventricle axis into a more accurate determination of the ventricle axis. A ventricle apex redefining processor redefines the ventricle apex approximation in accordance with the redefined ventricle axis. An iterative processor controls the ventricle axis redefining processor to redefine the ventricle axis in accordance with the redefined ventricle apex and the ventricle apex redefining processor to redefine the ventricle apex in accordance with the redefined ventricle axis.

In accordance with another aspect of the present invention a method for determining physiological characteristics of a patient's heart from a digital diagnostic image representation is disclosed. The diagnostic image representation is processed to obtain a heart blood volume image representation. A ventricle apex of one of the ventricles is approximated. A long axis of the ventricle is approximated as a line which intersects the ventricle apex. The ventricle axis is redefined into a more accurate determination of the ventricle axis. The ventricle apex is redefined in accordance with the redefined ventricle axis. A redefinement is repeated by an iterative processor, which controls the ventricle axis redefinement to redefine the ventricle axis in accordance with the redefined ventricle apex and the ventricle apex redefinement to redefine the ventricle apex in accordance with the redefined ventricle axis.

One advantage of the present invention is that it is completely automatic and free from operator subjectivity.

Another advantage of the present invention is that it is repeatable.

Another advantage resides in its precision and accuracy.

Another advantage resides in its speed and simplicity.

Other advantages include that it is not affected by myocardial disease or non-homogeneity and does not assume ventricle symmetry. The technique also expedites the generation of short axis slices along the ventricle.

Still further advantages and benefits of the present invention will become apparent to those of ordinary skill in the art upon reading and understanding the following detailed description of the preferred embodiments.

The invention may take form in various components and arrangements of components, and in various steps and arrangements of steps. The drawings are only for purposes of illustrating the preferred embodiments and are not be construed as limiting the invention.

Figure 1:
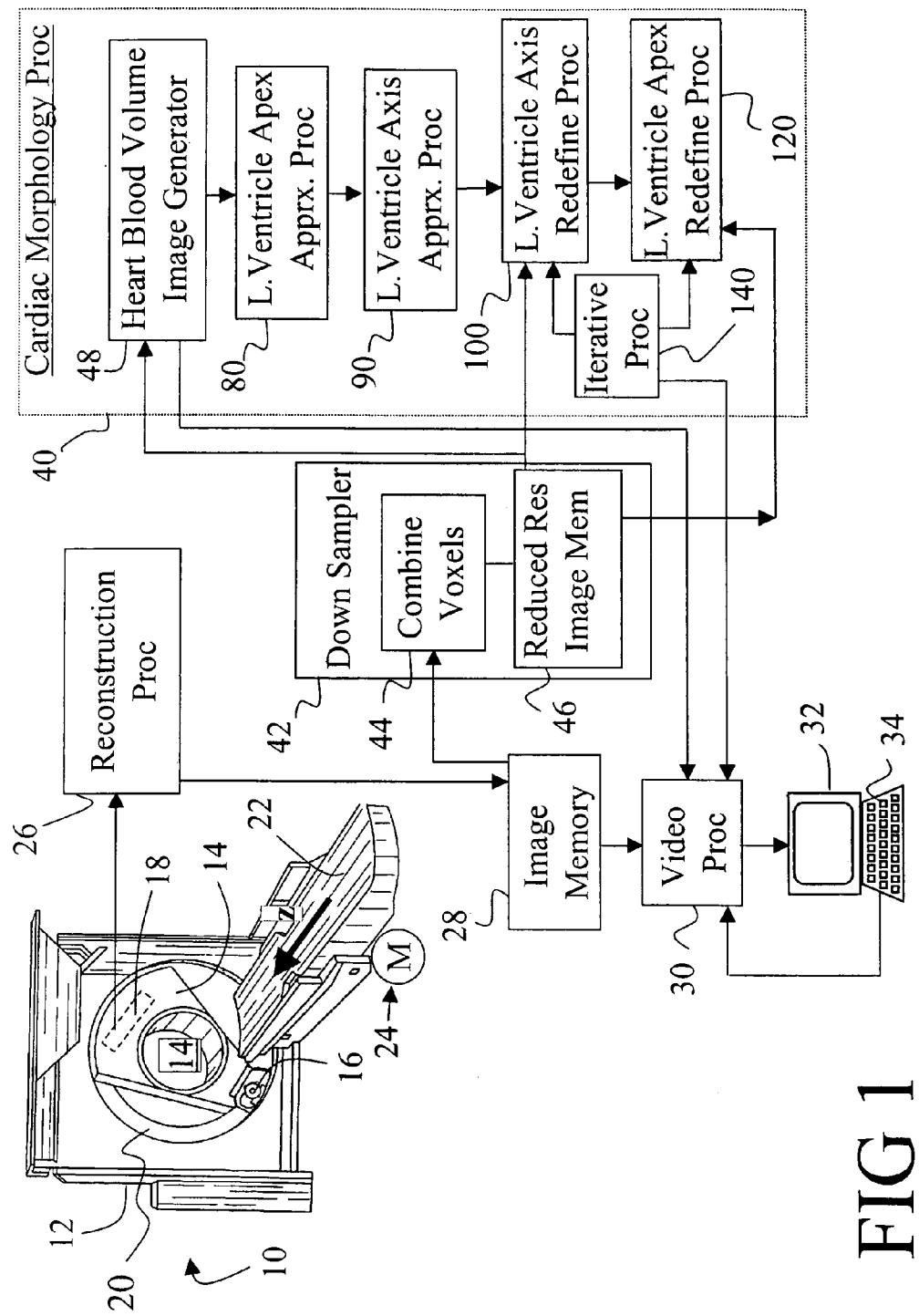
FIG. 1 is a diagrammatic illustration of a diagnostic imaging system in accordance with the present invention.

With reference to FIG. 1, a diagnostic imaging apparatus 10 generates electronic diagnostic image representations. In the preferred embodiment, the diagnostic imaging apparatus 10 is a CT scanner which generates a three-dimensional volumetric image representation which is made up of voxels whose position is defined along orthogonal axes. Other diagnostic imaging systems, such as magnetic resonance imaging, PET imaging, SPECT imaging, and other diagnostic techniques which generate analogous two or three-dimensional diagnostic images are also contemplated.

In the preferred embodiment, the CT scanner, includes a stationary gantry 12, in which a rotating gantry 14 is mounted. The rotating gantry carries an x-ray tube 16 and an array of detectors 18, which are diametrically opposed to each other across a scan circle or an examination region 20. Preferably, the detector array 18 is a two-dimensional detector array. A patient support 22 supports a region of interest of the subject in the examination region 20. A longitudinal drive motor 24 moves the patient support 22 longitudinally through the examination region 20. Preferably, the patient support 22 longitudinally reciprocates the subject as the rotating gantry 14 rotates continuously to generate a volumetric image representation of a transverse volume of the patient, which includes the patient's heart, or other region of interest. Alternately, the patient support 22 can be stepped and data can be collected along a series of parallel, transverse slices. Although the detector array 18 is illustrated as rotating with the rotating gantry 14, the detector array 18 may optionally be mounted as a continuous ring on the stationary gantry 12.

A three-dimensional reconstruction processor 26 reconstructs the output signals from the detector array 18 in accordance with the angular position of each detector element, the angular position of the x-ray tube 16, and the longitudinal position of the patient support 22 at the time of sampling into one or more three-dimensional image representations. For simplicity of illustration, the present application describes imaging a single volume of a selected phase of the cardiac cycle. However, it is contemplated that a volumetric image representation can be made at a plurality of selected phases of the cardiac cycle and that such images can be made over several cardiac cycles. The reconstructed image representation is stored in a volumetric image memory 28.

A video processor 30 is connected with the image memory for retrieving planar imaging slices from the volumetric image representation and displaying them on a monitor 32. A user input device 34, such as a keyboard, enables the user to control the video processor 30 to display selected sagittal, transverse, and longitudinal slices, oblique image slices, 3D projections, and the like.

With continuing reference to FIG. 1, a cardiac morphology determining processor or means 40 extracts selected portions of the volumetric image representation of the selected cardiac phase and generates physiological information about the physiology of the patient's left ventricle or other portions of the patient's heart or anatomy. Because the volumetric image representation typically has a resolution, which is more precise than the resolution with which the left ventricle axis needs be determined, a downsampling means or processor 42 reduces the number of voxels in each direction, by a factor of two in the preferred embodiment. That is, 2×2×2 cubes of data from the volumetric image representation are combined into a single voxel by a voxel combining means 44. In this example, voxels with 0.5 mm resolution in the volumetric image representation are reduced to voxels of 1 mm resolution. Other downsampling ratios are also contemplated. Further, where greater measurement resolution is needed or where speed is not a consequence, the downsampling can be eliminated. The reduced resolution image is stored in a reduced resolution image memory 46.

Figure 2:
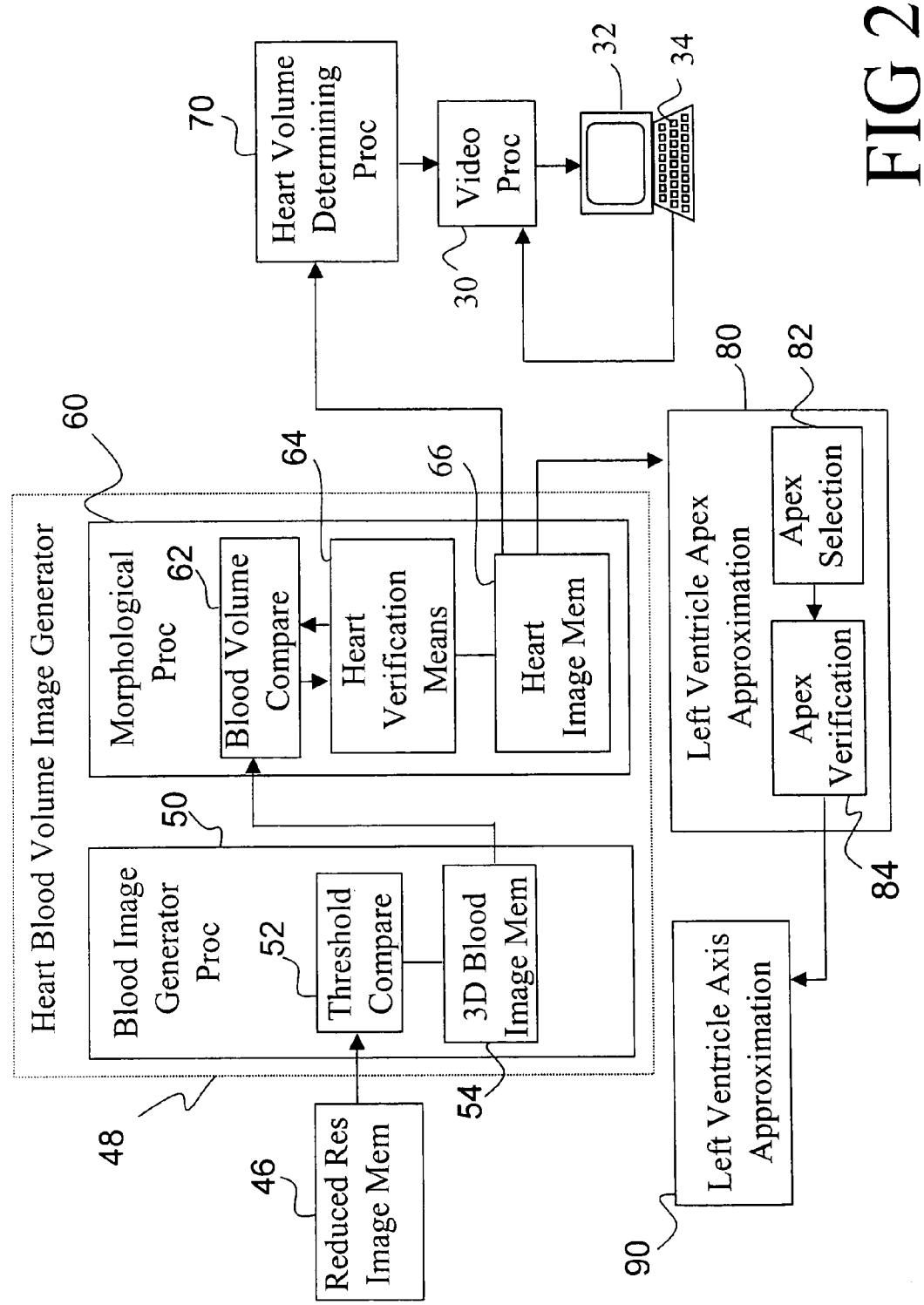
FIG. 2 depicts a diagrammatic representation of a subsystem for generating a heart image and making a first approximation of left ventricle apex and left ventricle axis.

With reference to FIG. 2 and continuing reference to FIG. 1, a heart blood volume image generating processor or means 48 generates an image of the blood volume of the patient's heart. First, a blood image generating means or processor 50 generates an image of all blood and, if applicable bones, in the region of interest with the surrounding tissue removed. More specifically to the preferred embodiment, a threshold means or step 52 compares the gray scale value or CT number of each voxel with the gray scale or CT numbers for blood. Those in the appropriate gray scale or CT number range for blood are retained and preferably set to a common gray scale value. The remaining voxels are zeroed. In this manner, a 0 and 1 or black/white three-dimensional image representation of the blood in the imaged region is generated for storage in a 3D blood image memory or buffer 54.

A morphological means or processor 60 identifies the heart chambers and eliminates the remainder of the blood volume and bones from the image to generate a heart chamber image. The 3D blood image is a volumetric image representation of the circulatory system and other organs and regions of the body within the imaging region which have a large concentration of blood. Due to the downsizing, small blood vessels have been eliminated and the image representation is dominated by several larger blood pools which can represent the heart, aneurysms, other organs that hold large volumes of blood, bones, and the like. Typically, the heart is the largest blood volume. A volume size determining and comparing means 62 determines the relative size of the various blood volumes and selects the largest. The largest blood volume is retained as the image of the blood space in the heart and the remainder of the blood regions and bones are discarded. The three-dimensional image representation of the blood regions of the heart are stored in a heart blood image memory or buffer 64.

One technique for verifying that the identified blood volume belongs to the heart includes looking for changes in the above volume or its boundaries over time. The ventricular volume will change over time being maximal at end diastole (corresponding to the R-wave on the ECG) and minimal about 40-50% through the cycle (end systole).

With continuing reference to FIG. 2, a heart volume determining processor or means 70 determines the total volume of blood in the heart. In the preferred embodiment, the heart volume is determined by counting the number of voxels in the heart blood volume image from the heart blood volume image memory or buffer 64. The number of blood voxels in the image is multiplied by the volume corresponding to each voxel to determine the heart volume. This heart volume information is supplied to the video processor 30 to be converted into appropriate form for display on the monitor 32. The heart volume information also assists in approximating long axis length and in short axis generation.

Figure 3:
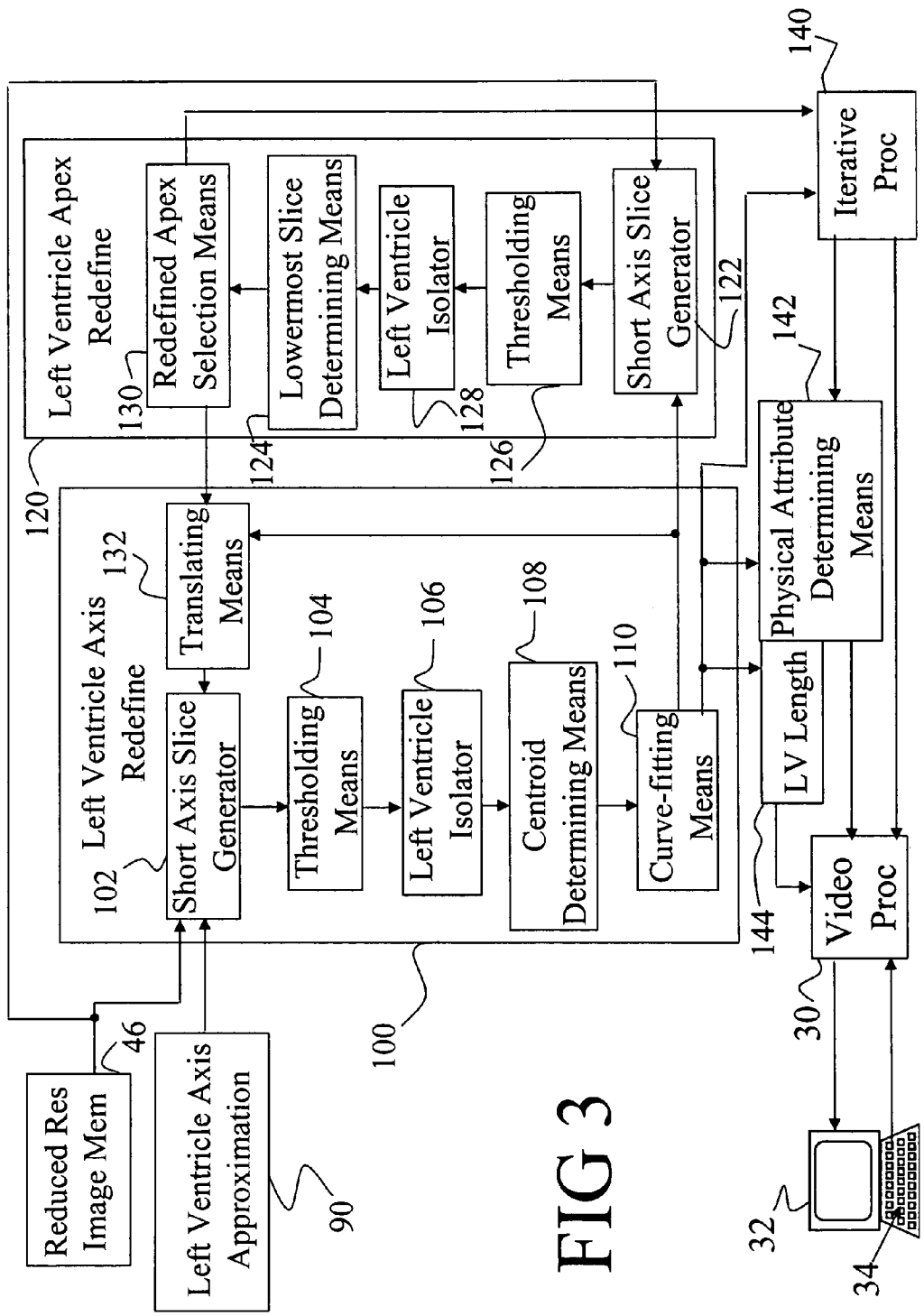
FIG. 3 depicts a diagrammatic representation of a subsystem for redefining the left ventricle apex and left ventricle axis.

With continuing reference to FIG. 2 and particular reference to FIG. 3, a left ventricle apex determining means or processor 80 determines the location of the apex of the left ventricle. In the human anatomy, the left ventricle is an elongated structure, which typically terminates in a pointed or conical end. Normally, the left ventricle is on the left side of the patient and more posterior than the right ventricle. In the preferred embodiment, an apex selection means 82 selects the left ventricle apex as the point which is the furthest from the upper right anterior corner of the imaged volume. Other ways of selecting the first approximation of the apex are also contemplated, such as looking towards the left lower posterior most point in the heart volume image. Optionally, a verification means or routine 84 confirms that the apex selection technique or means 82 has identified a point on the left ventricle. The verification means 84 checks to make sure that there is a large mass of blood to the right of the selected left ventricle apex, thus confirming that the selected apex is indeed a portion of the left ventricle. Additionally, the verification means 84 looks to the left of the identified apex to see if there is a large pool of blood there, which would suggest that the left ventricle is still further left and that a point on the right ventricle has been inadvertently selected.

Next, a left ventricle axis approximating means or processor 90 generates a first approximation of the left ventricle axis. In the preferred embodiment, the first approximation of the left ventricle axis is defined as a line, which intersects the left ventricle apex and slopes to the right at a preselected angle of 30° and antiriorly at a preselected angle up to 30°.

A left ventricle axis redefining means or technique 100 redefines the left ventricle axis to make the definition more accurate. More specifically to the preferred embodiment, a series of short axis slices through the downsampled image from the reduced resolution image memory 46 are generated. That is, a short axis slice generating processor or means 102 generates a series of lower resolution slices which are orthogonal to the approximated left ventricle axis. A thresholding means or technique 104 thresholds these short axis slices to convert them into blood images. A left ventricle isolating means or step 106 identifies the pool of blood surrounding the approximation of the left ventricle axis as the left ventricle. The portions of the blood image data corresponding to the right ventricle and other surrounding tissue are eliminated such that each short axis slice represents only the left ventricle. A centroid determining means or technique 108 determines the centroid of each of the short axis left ventricle slices. A curve-fitting means or technique 110 redefines the left ventricle axis as the line which is a best fit through the centroids of the short axis left ventricle slices, which line also passes through the most recent approximation of the left ventricle apex.

Once the left ventricle axis redefining means 100 has redefined the left ventricle axis, a left ventricle apex redefining means 120 redefines the position of the left ventricle apex. In the preferred embodiment, a short axis slice means or technique 122 generates a series of short axis slices perpendicular to the redefined left ventricle axis. The short axis slices are monitored by a lowermost slice determining means 124 that determines the short axis slice that is lowermost along the axis and has at least one voxel identified as blood. To simplify this process, each of the generated short axis slices are thresholded by thresholding means 126 to a blood only image and the left ventricle is isolated by a left ventricle isolator 128 as described above. If the lowermost slice has a single voxel of blood, then the voxel is selected as the new apex by a redefined apex selection means 130. If the lowermost slice has a plurality of blood voxels, then the location of the axis is selected by measuring the centroid of the plurality of blood voxels or other appropriate techniques. Alternatively, rather than thresholding the low resolution image in each iteration, the left ventricle axis and apex redefining means 100, 120 can work with the blood volume image from the memory 64.

Once the apex has been redefined, the left ventricle axis redefining means or technique 100 redefines the left ventricle axis. More specifically, the left ventricle axis redefining means 100 redefines the left ventricle axis as passing through the redefined apex. More specifically to the preferred embodiment, the left ventricle axis redefining means includes a means or technique 132 for shifting the previously determined left ventricle axis so that it passes through the redefined left ventricle apex. Then, the left ventricle axis redefining technique described above is repeated. Alternately, other techniques for bringing the left ventricle axis in compliance with the new left ventricle apex are contemplated. For example, the left ventricle apex can be redefined as the line passing through the new apex which is also a best fit to the centroid points that were determined at step or means 108. Various other techniques for causing the left ventricle axis to be redefined to pass through the redefined apex are also contemplated.

The left ventricle axis redefinement and left ventricle apex redefinement are repeated until the left ventricle axis and apex converge on a solution, i.e., do not change more than a preselected maximum with each iteration. In practice, it has been found that this technique converges in two or three repetitions so reliably that the process can be terminated based on the number of iterations rather than by determining convergence. Once an end determining means or technique 140 has determined that the solution has converged or that the requisite number of iterations has been completed, it forwards the most recent redefinement of the left ventricle axis and apex to the video processor for conversion into appropriate form for display on the video monitor 32. A significant physical attribute determining means or processor 142 prepares the final image(s) for examination and evaluation of significant physical attributes related to left ventricle geometry and functioning. The physical attribute determining means includes a length determining means 144 as well as means for determining the other physical attributes of interest to the diagnosing physician. The length and other significant physical attribute information is forwarded to the video processor for numerical display. In one optional form of this display, the video processor retrieves an oblique slice that is coplanar with the determined left ventricle axis and displays such slice on the monitor 32 along with the length of the axis, vector trajectory of the axis, cardiac phase of the image, and other information as may be appropriate to the diagnostician. Short axis images orthogonal to the long axis and other significant information and attributes can also be displayed.

Although described with reference to CT, it will be appreciated that various other types of diagnostic scanners including MRI, nuclear, echo, electrochemical mapping, and contrast ventriculography are also contemplated. Further, although described with reference to the left ventricle, the technique is equally applicable to the right ventricle cavity. Of course, some of the described directions will be reversed since the left ventricle is typically left and posterior; whereas the right ventricle is typically right and anterior. Further, ventricle axes can be determined at several portions of the cardiac cycle, such as the end diastole when the left ventricle is the largest, and the end systole when the left ventricle is at its smallest. Intermediate portions of the cardiac cycle are also contemplated. The technique is also contemplated to measure other volumes or structures. Also calculations of ventricular volume and short axis area at different points over the cardiac cycle enable automatic determination of the maximum (end diastole) and minimum (end systole) volumes. Note that thresholding can be gauged to select a specific organ, rather than blood.

The invention has been described with reference to the preferred embodiments. Modifications and alterations will occur to others upon a reading and understanding of the preceding detailed description. It is intended that the invention be construed as including all such modifications and alterations insofar as they come within the scope of the appended claims or the equivalents thereof.

Having thus described the preferred embodiments, the invention is now claimed to be:

1. A morphological apparatus for determining physiological characteristics of a patient's heart from a digital diagnostic image representation, the apparatus comprising:
   a means for processing the diagnostic image representation into a heart blood volume image representation, which depicts interior volumes of the patient's heart;
   a ventricle apex approximating means for determining an approximation of an apex of one of the ventricles from the heart blood volume image representation,
   wherein the ventricle apex approximating means includes a selector means for selecting a region of the image representation that is left, posterior, and down;
   a ventricle axis approximating means for determining an approximation of an axis of the ventricle, which intersects the ventricle apex;
   a ventricle axis redefining means for redefining the approximation of the ventricle axis into a more accurate determination of the ventricle axis;
   a ventricle apex redefining means for redefining the ventricle apex approximation in accordance with the redefined ventricle axis; and
   an iterative repeating means which alternately controls the ventricle axis redefining means to redefine the ventricle axis in accordance with the redefined ventricle apex and the ventricle apex redefining means to redefine the ventricle apex in accordance with the redefined ventricle axis.

2. The apparatus as set forth in claim 1, further including:
   a diagnostic imaging means which examines a cardiac region of a patient and generates the image representation in accordance with the examination.

3. The apparatus as set forth in claim 1, further including:
   a down sampling means for reducing the resolution of the image representation before the heart blood volume imaging means generates the heart blood volume image representation.

4. The apparatus as set forth in claim 1, wherein the heart blood volume imaging means includes:
   a means for eliminating non-blood tissue from the image representation to generate an image representation of patient blood; and
   a means for identifying a portion of the blood image corresponding to the patient's heart.

5. The apparatus as set forth in claim 4, wherein the identifying means also identifies bone.

6. The apparatus as set forth in claim 4, wherein:
   the blood image generating means includes a thresholding means for retaining voxels of the image representation corresponding to blood and discarding voxels of the image representation corresponding to other tissues, and
   the heart identifying means includes a comparing means, which determines a blood pool of greatest volume.

7. The apparatus as set forth in claim 6 further including:
   a verification means for examining the boundaries of the blood pool for a change over time which corresponds to cardiac pulsing.

8. The apparatus as set forth in claim 4, further including a heart volume determining means, which determines a volume of the heart image.

9. The apparatus as set forth in claim 1 wherein the ventricle apex approximating means includes:
   a means for selecting a point of the heart image representation, which is most left, posterior, and down.

10. The apparatus as set forth in claim 9, further including:
    a means for verifying that the selected point is in the left ventricle by one of:
    checking for another blood pool to the left of the selected point in the heart image, and
    checking for a blood pool to the right of the selected point in the heart image.

11. The apparatus as set forth in claim 1, wherein the ventricle axis approximating means assigns a trajectory of a preselected angle, which passes through the ventricle apex approximation as the ventricle axis approximation.

12. The apparatus as set forth in claim 1, wherein the ventricle axis redefining means includes:
    a short axis slice means, which generates a plurality of slice image representations orthogonal to one of the axis approximation and a prior redefined axis;
    an isolating means, which isolates a selected one of the ventricles in the slice images;
    a centroid means, which determines a centroid in each of the ventricle slice images, which represents a centroid of the area of the ventricle in each corresponding slice image; and
    a curve fitting means, which generates a best fit line through the centroids and a most recent one of the apex approximation and a redefined apex.

13. The apparatus as set forth in claim 12, wherein the short axis slice means generates slices through the image representation and further including:
    a thresholding means for thresholding the short axis slices to limit each slice to a representation of blood only.

14. The apparatus as set forth in claim 1, wherein the ventricle apex redefining means includes:
    a short axis slice determining means for determining a series of slice image representations perpendicular to the redefined ventricle axis; and
    a means for determining a lowermost one of the short axis slices, which intersects the ventricle, the point of intersection of the lowermost slice and the ventricle being designated as a most recently redefined apex.

15. The apparatus as set forth in claim 14, wherein the ventricle axis redefining means further includes:
    a translating means for translating the most recently redefined axis to intersect the most recently redefined apex.

16. A method for determining physiological characteristics of a patient's heart from a digital diagnostic image representation, the method comprising:
    processing the diagnostic image representation into a heart blood volume image representation, which depicts interior volumes of the patient's heart;
    determining an approximation of an apex of one of the ventricles by selecting a region of the image representation that is left, posterior, and down;
    determining an approximation of an axis of the ventricle, which intersects the ventricle apex;
    redefining the approximation of the ventricle axis into a more accurate determination of the ventricle axis;
    redefining the ventricle apex approximation in accordance with the redefined ventricle axis; and
    alternately controlling redefining of the ventricle axis in accordance with the redefined ventricle apex and redefining of the ventricle apex in accordance with the redefined ventricle axis.

17. The method as set forth in claim 16, further including:
examining a cardiac region of a patient; and
generating the image representation in accordance with the examination.

18. The method as set forth in claim 16, further including:
reducing the resolution of the image representation before generating the heart blood volume image representation.

19. The method as set forth in claim 16, wherein the step of generating the heart blood volume image representation includes:
eliminating non-blood tissue from the image representation to generate an image representation of patient blood; and
identifying a portion of the blood image corresponding to the patient's heart.

20. The method as set forth in claim 19 further including:
verifying that the identified portion of the blood image expands and contracts in accordance with a cardiac cycle.

21. The method as set forth in claim 19, wherein the step of generating the blood image includes:
retaining voxels of the image representation corresponding to blood, and
discarding voxels of the image representation corresponding to other tissues; and the step of identifying the heart includes:
determining a blood pool of greatest volume.

22. The method as set forth in claim 19, further including:
determining a volume of the heart image.

23. The method as set forth in claim 16, wherein the step of determining the ventricle apex approximation includes:
selecting a point of the heart image representation, which is most left, posterior, and down.

24. The method as set forth in claim 23, further including:
verifying that the selected point is in the left ventricle by one of:
checking for another blood pool to the left of the selected point in the heart image, and
checking for a blood pool to the right of the selected point in the heart image.

25. The method as set forth in claim 16, wherein the step of determining the ventricle axis approximation includes:
assigning a trajectory of a preselected angle, which passes through the ventricle apex approximation, as the ventricle axis approximation.

26. The method as set forth in claim 16, wherein the step of redefining the ventricle axis includes:
generating a plurality of slice image representations orthogonal to one of the axis approximation and a prior redefined axis;
isolating a selected one of the ventricles in the slice images;
determining a centroid in each of the ventricle slice images; and
generating a best fit line through the centroids and one of the apex approximation and a redefined apex.

27. The method as set forth in claim 26, further including:
generating slices through the image representation; and
thresholding the short axis slices to limit each slice to a representation of blood only.

28. The method as set forth in claim 16, wherein the step of redefining the ventricle apex includes:
determining a series of slice image representations perpendicular to the redefined ventricle axis; and
determining a lowermost one of the short axis slices, which intersects the ventricle, the point of intersection of the lowermost slice and the ventricle being designated as the redefined apex.

29. The method as set forth in claim 28, further including:
translating the redefined axis to intersect the redefined apex.

30. A morphological system for determining physiological characteristics of a selected patient organ from a digital diagnostic image representation, the system comprising:
a thresholding processor, which thresholds the diagnostic image representation in accordance with CT numbers representation of the selected organ and removing tissue of other CT numbers to generate a selected organ image;
an apex approximation processor, which initially determines an approximation of an apex of the selected organ image by selecting a region of the image representation that is left, posterior, and down;
an axis approximation processor, which initially determines an approximation of an axis of the organ, which axis intersects the apex;
an axis redefining processor, which redefines the approximation of the axis into a more accurate determination of the organ axis;
an apex redefining processor, which redefines the apex approximation in accordance with the redefined axis; and
an iterative processor, which controls the axis redefining processor to redefine the organ axis in accordance with the redefined apex and the apex redefining processor to redefine the apex in accordance with the redefined organ axis.

* * * * *